United States Patent [19]

Nakano et al.

[11] Patent Number: 4,740,374

[45] Date of Patent: Apr. 26, 1988

[54] ANTI-INFLAMMATORY ANALGESIC ADHESIVE PREPARATION

[75] Inventors: Yoshihisa Nakano; Kazuhisa Ninomiya; Tetuo Horiuchi; Yuichi Inoue, all of Osaka, Japan

[73] Assignee: Nitto Electric Industrial Co., Ltd., Osaka, Japan

[21] Appl. No.: 917,136

[22] Filed: Oct. 9, 1986

[30] Foreign Application Priority Data

Nov. 26, 1985 [JP] Japan ................................. 60-265788

[51] Int. Cl.$^4$ ............................................. A61F 13/02
[52] U.S. Cl. ..................................... 424/448; 424/449
[58] Field of Search ................................ 424/448, 449

[56] References Cited

FOREIGN PATENT DOCUMENTS 0042290 6/1981 European Pat. Off. .
0156080 12/1984 European Pat. Off. .

Primary Examiner—Thurman K. Page
Assistant Examiner—L. R. Horne
Attorney, Agent, or Firm—Sughrue, Mion, Zinn, Macpeak & Seas

[57] ABSTRACT

An anti-inflammatory analgesic adhesive preparation is disclosed, comprising a flexible support having laminated thereon a pressure-sensitive adhesive material layer which contains a non-steroidal anti-inflammatory analgesic agent having salt form and an organic acid. This adhesive preparation has excellent percutaneous absorption properties.

12 Claims, No Drawings

ANTI-INFLAMMATORY ANALGESIC ADHESIVE PREPARATION

FIELD OF THE INVENTION

The present invention relates to an anti-inflammatory analgesic adhesive preparation having excellent percutaneous absorption properties.

BACKGROUND OF THE INVENTION

Non-steroidal anti-inflammatory analgesic agents do not exhibit such serious side effects as exhibited in steroidal anti-inflammatory analgesic agents, and are widely used in a clinical field.

However, these non-steroidal anti-inflammatory analgesic agents have a disadvantage to still cause various side effects such as gastro-intenstinal lesion although not to the extent that is caused by steroidal anti-inflammatory analgesic agents. In order to minimize such side effects, various dosage forms are now under extentisve investigation.

Recently, in order to overcome the above problems on side effects and maintain the drug effects for a long period of time, an administration method to percutaneously absorb the effective component is being watched. Various ointments and adhesive preparations containing an effective component so as to practically employ the administration method have been developed.

However, the skin has a stratum corneum containing keratin as a major component and further contains a large amount of a fat-soluble component such as fat, wax and cholesterol. Therefore, the skin has a physiological defensive function, a so-called "barrier function", and as a result, it is difficult to easily make a percutaneous absorption of a drug.

In particular, many of non-steroidal anti-inflammatory analgesic agents, the utility of which is highly valued, have a salt form, and the skin exhibits a strong barrier function against drugs having a salt form.

On the other hand, skin adhesive preparations are composed of a pressure-sensitive adhesive material comprising a rubber or acrylic high molecular weight material as a base material. These materials generally do not dissolve drugs sufficiently, and it is quite difficult to uniformly dissolve the drug having the salt form and maintain the dissolved state. Even if the drug in the skin adhesive preparation is prepared in the dissolved state, crystallization of the drug contained occurs during the storage, sometimes inhibiting the percutaneous absorption of the drug.

SUMMARY OF THE INVENTION

As a result of extensive investigations on an adhesive preparation which overcomes the above disadvantages, and increases the solubility and percutaneous absorption of non-steroidal anti-inflammatory analgesic agent having a salt form, thereby exhibiting the effect in treating disease, it has been found that if a non-steroidal anti-inflammatory analgesic agent having a salt form is contained in a pressure-sensitive adhesive material layer in combination with an organic acid, the solubility of the non-steroidal anti-inflammatory analgesic agent having a salt form in the pressure-sensitive adhesive material increases and the transfer of the drug to the skin surface is facilitated, whereby the non-steroidal anti-inflammatory analgesic agent can easily penetrate through the stratum corneum as a barrier layer.

An object of the present invention is to provide an anti-inflammatory analgesic adhesive preparation having high percutaneous absorption properties of a non-steroidal anti-inflammatory analgesic agent having a salt form.

Another object of the present invention is to provide an anti-inflammatory analgesic adhesive preparation in which a non-steroidal anti-inflammatory analgesic agent having a salt form is uniformly dissovled in a pressure-sensitive adhesive material.

The anti-inflammatory analgesic adhesive preparation of the present invention comprises a flexible support having laminated thereon a pressure-sensitive adhesive material layer containing a non-steroidal anti-inflammatory analgesic agent having a salt form and an organic acid.

DETAILED DESCRIPTION OF THE INVENTION

The term "a non-steroidal anti-inflammatory analgesic agent having a salt form" used herein excludes Dichlofenac Sodium. Therefore, unless otherwise indicated, the term "non-steroidal anti-inflammatory analgesic agent having a salt form" is defined to exclude Dichlofenac Sodium.

The pressure-sensitive adhesive material layer which can be used in the present invention is a layer containing and maintaining a non-steroidal anti-inflammatory analgesic agent having a salt form as an effective component and an organic acid as an additive to increase solubility and percutaneous absorption of the non-steroidal anti-inflammatory analgesic agent having a salt form. The material for such layer is not particularly limited so long as it is a material capable of achieving the above objects and it is a layer made of a material capable of adhering to the skin surface.

High molecular weight adhesive materials can be used as the pressure-sensitive adhesive materials. Examples of the materials are acrylic pressure-sensitive adhesive materials; rubbers such as silicone rubber, polyisoprene rubber, polyisobutylene rubber, polybutadiene, styrene-butadiene (or isoprene)-styrene block copolymer rubber, acrylic rubber and natural rubber; vinyl-based high molecular weight materials such as polyvinyl alkyl ether, polyvinyl acetate, a partially saponified product of polyvinyl acetate, polyvinyl alcohol and polyvinyl pyrrolidone; cellulose derivatives such as methyl cellulose, carboxylmethyl cellulose and hydroxypropyl cellulose; polysaccharides such as pullulan, dextrin and agar; polyurethane elastomers; and polyester elastomers.

Of these compounds, acrylic pressure-sensitive adhesive materials are preferred from standpoints of adhesive properties to the skin and stability of the drug. In particular, pressure-sensitive adhesive materials comprising copolymers of an alkyl ester of (meth)acrylic acid, an alkyl ester of (meth)acrylic acid containing an ether bond in the molecule and copolymerizable monomers other than the above-described monomers are used as materials having low skin irritating properties and solubility of the drugs.

Examples of acrylic pressure-sensitive adhesive materials selected from the standpoints of adhesive properties to the skin and stability of the drug are homo- or copolymers of at least one of alkyl esters of (meth)acrylic acid such as butyl (meth)acrylate, pentyl (meth)acrylate, hexyl (meth)acrylate, heptyl (meth)acrylate, octyl (meth)acrylate, nonyl (meth)acrylate, decyl (meth)a- crylate, undecyl (meth)acrylate, dodecyl (meth)acrylate, and tridecyl (meth)acrylate, and copolymers of at least one of the above esters and other monomers copolymerizable therewith.

Examples of the copolymerizable monomer include carboxyl group-containing monomers such as (meth)acrylic acid, itaconic acid, crotonic acid, maleic acid, maleic anhydride and fumaric acid; sulfoxyl group-containing monomers such as styrenesulfonic acid, arylsulfonic acid, sulfopropyl acrylate, (meth)acryloyloxynaphthalenesulfonic acid, acrylamidomethylpropanesulfonic acid and acryloyloxybenzenesulfonic acid; hydroxyl group-containing monomers such as hydroxyethyl (meth)acrylate and hydroxypropyl (meth)acrylate; amide group-containing acrylic monomers such as (meth)acrylamide, dimethyl(meth)acrylamide, N-butylacrylamide, tetramethylbutylacrylamide and N-methylol(meth)acrylamide; alkylaminoalkyl group-containing acrylic monomers such as aminoethyl (meth)acrylate, dimethylaminoethyl (meth)acrylate, diethylaminoethyl (meth)acrylate and tertbutyl (meth)acrylate; alkyl esters of acrylic acid containing an ether bond in the molecule thereof such as methoxyethyl (meth)acrylate, ethoxyethyl (meth)acrylate, butoxyethyl (meth)acrylate, tetrahydrofurfuryl (meth)acrylate, methoxyethylene glycol (meth)acrylate, methoxydiethylene glycol (meth)acrylate, methoxypolyethylene glycol (meth)acrylate and methoxypolypropylene glycol (meth)acrylate; vinyl monomers such as N-(meth)acryloylamino acid; functional monomers such as acrylic monomers such as urethane, urea or isocyanate ester of acrylic acid; and vinyl monomers such as (meth)acrylonitrile, vinyl acetate, vinyl propionate, vinyl pyrrolidone, vinyl pyridine, vinyl pyrazine, vinyl piperadine, vinyl piperidone, vinyl pyrimidine, vinyl pyrrole, vinyl imidazole, vinyl caprolactam, vinyl oxazole, vinyl thiazole, vinyl morpholine, styrene, α-methylstyrene and bis(N,N'-dimethylaminoethyl) maleate.

The above alkyl esters of (meth)acrylic acid and copolymerizable monomers include isomers in which the alkyl portion is straight or branched, and isomers and derivatives in which the position of substituents is different.

It is desirable from a standpoint of the balance between adhesive properties to the skin and cohesion that the ratio of the alkyl ester of (meth)acrylic acid to the copolymerizable monomer in the acrylic pressure-sensitive adhesive material is 50:50 to 99:1 by weight. When alkyl esters of (meth)acrylic acid containing an ether bond in the molecule thereof are used from the standpoint of the low skin irritating properties, it is desirable that the ratio of the alkyl ester of (meth)acrylic acid/the alkyl ester of (meth)acrylic acid containing an ether bond in the molecule/the other copolymerizable monomer is 40 to 80/59 to 10/1 to 40.

When the above composition is used, in the case where there is a trouble that after adhering to the skin, it causes the phenomenon of adhesive transfer on the applied skin, thereby contaminating the skin surface, it is preferred that the composition is subjected to suitable chemical crosslinking treatment (e.g., copolymerization of crosslinkable monomers and addition of a crosslinking agent) or physical crosslinking treatment (e.g., irradiation with ultraviolet rays and ionizing radiations such as electron beam) to such an extent of not deteriorating the adhesive properties to the skin.

As salts in the non-steroidal anti-inflammatory analgesic agent having a salt form which can be used in the present invention, any salts can be used so long as they are pharmaceutically acceptable. For example, alkali metal salts, alkaline earth metal salts, aluminum salts and the like are preferred. Examples thereof are the salts of indomethacin, flufenamic acid, mefenamic acid, tolfenamic acid, meclofenamic acid, ibuprofen, bucolome, alclofenac, amfenac, zomepirac, flurbiprofen, tolmetin, ketoprofen, naproxen, fenbufen, protizinic acid, pranoprofen, sulindac, loxoprofen, fenoprofen, tiaprofenic acid, diflunisal and fentiazac. Of those salts, tolmetin sodium, fenoprofen calcium, sodium meclofenamate, amfenac sodium, zomepirac sodium, loxoprofen sodium and aluminum flufenamate are particularly preferred.

The amount of the non-steroidal anti-inflammatory analgesic agent having a salt form which is compounded in the pressure-sensitive adhesive material is not limited so long as the therapeutic effect is exhibited. The amount of the non-steroidal anti-inflammatory analgesic agent having a salt form compounded in the pressure-sensitive adhesive material is generally 1 to 40 wt%, and preferably 5 to 30 wt%, based on the weight of the pressure-sensitive adhesive material, and 20 to 1,600 $\mu g/cm^2$, and preferably 100 to 1,200 $\mu g/cm^2$ per unit area.

Since the non-steroidal anti-inflammatory analgesic agent used in the present invention is in a salt form, it is difficult to dissolve a large amount of the non-steroidal anti-inflammatory analgesic agent in the pressure-sensitive adhesive material layer having relatively high lipophilic properties and maintain the agent therein. Even if a large amount of the non-steroidal anti-inflammatory analgesic agent is incorporated, in some cases all the drug cannot be dissolved or crystallization of the drug occurs, making it impossible to diffuse a sufficient amount of the drug to the skin surface.

The present invention overcomes this problem by concurrently using an organic acid. The use of the organic acid increases the solubility of the non-steroidal anti-inflammatory analgesic agent having a salt form in the pressure-sensitive adhesive material layer and also the percutaneous absorption properties.

It is believed that the reason for this is that since by concurrently using the non-steroidal anti-inflammatory analgesic agent having a salt form and the organic acid, the non-steroidal anti-inflammatory analgesic agent is converted into free-based drug having higher oleophilicity, the solubility of the drug in the pressure-sensitive adhesive material layer is increased and the drug can easily penetrate through the stratum corneum having the barrier function, viz., the percutaneous absorption properties are increased.

As such organic acids, it is preferred to use acids stronger than free-based non-steroidal anti-inflammatory analgesic agent, and carboxylic acids are particularly preferred. Examples of carboxylic acids include citric acid, succinic acid, tartaric acid, maleic acid, fumaric acid, salicylic acid and acetic acid. Citric acid, succinic acid and tartaric acid are particularly preferred.

The amount of the organic acid added in the pressure-sensitive adhesive material layer is from 5 to 100 parts by weight, preferably from 10 to 50 parts by weight, per 100 parts by weight of the non-steroidal anti-inflammatory analgesic agent having a salt form.

As a support on which the pressure-sensitive adhesive material layer containing the non-steroidal anti-inflammatory analgesic agent having a salt form and organic acid is provided, a material having a flexibility is chosen in order to conform to the movement of the skin surface. Examples of the supports are a plastic film, nonwoven fabrics, woven fabrics, paper, a metallic foil, a foamed film or combinations thereof.

As described above, in the anti-inflammatory analgesic adhesive preparation of the present invention, the organic acid which is compounded in the pressure-sensitive adhesive material in combination with the non-steroidal anti-inflammatory analgesic agent having a salt form which is sparingly soluble in the pressure-sensitive adhesive material has an function of increasing the solubility of the drug in the pressure-sensitive adhesive material and increasing the percutaneous absorption properties of the drug.

Accordingly, in the anti-inflammatory analgesic adhesive preparation of the present invention, the non-steroidal anti-inflammatory analgesic agent having a salt form compounded in the adhesive is percutaneously absorbed easily, thereby effectively treating inflammation and painful diseases. Furthermore, since the preparation can be externally administered, the side effect is low and the therapeutic effect can be exhibited continuously.

The present invention is described in greater detail by reference to the following examples. The present invention, however, is not to be construed as limited to the following examples. In the examples, all parts are by weight unless otherwise indicated.

EXAMPLE 1

55 Parts of 2-ethylhexyl acrylate, 30 parts of methoxyethyl acrylate, 15 parts of vinyl acetate and 0.3 part of azobisisobutylonitrile were placed in a four-necked flask and the mixture was heated to a temperature of 60° to 63° C. in an inert gas atmosphere to initiate the polymerization reaction. The reaction was continued for 10 hours while controlling the reaction temperature by adding dropwise 125 parts of ethyl acetate. The reaction solution was further aged at 75° to 80° C. for 2 hours to prepare a copolymer solution.

To the copolymer solution thus obtained were added tolmetin sodium and citric acid in such amounts that the contents of tolmetin sodium and citric acid after drying were 20 wt% and 4 wt% based on the weight of the pressure-sensitive adhesive material layer, respectively, and the resulting mixture was coated on a releasing liner made of a polyester in such an amount that the drug content was 400 $\mu g/cm^2$ and then dried to prepare a pressure-sensitive adhesive material layer.

This pressure-sensitive adhesive material layer was transferred to a nonwoven fabric with an ethylene-vinyl acetate copolymer film (vinyl acetate content: 28 wt%) having a thickness of 40 $\mu m$ laminated thereon at the ethylene-vinyl acetate copolymer layer side to produce an anti-inflammatory analgesic adhesive preparation of the present invention.

EXAMPLE 2

The anti-inflammatory analgesic adhesive preparation was prepared in the same manner as in Example 1 except that amfenac sodium and maleic acid were added to the copolymer solution in such amounts that the contents of amfenac sodium and maleic acid after drying were 20 wt% and 4 wt%, respectively.

EXAMPLE 3

95 Parts of 2-ethylhexyl acrylate, 5 parts of acrylic acid and 0.2 part of benzoyl peroxide were placed in a four-necked flask and the mixture was heated to a temperature of 62° to 65° C. in an inert gas atmosphere to initiate the polymerization reaction. The reaction was continued for 8 hours while controlling the reaction temperature by adding dropwise 125 parts of ethyl acetate. The reaction solution was further aged for 2 hours at 75° to 80° C. to prepare a copolymer solution.

To the copolymer solution thus obtained were added loxoprofen sodium and succinic acid in such amounts that the contents of loxoprofen sodium and succinic acid after drying were 10 wt% and 3 wt% based on the weight of the pressure-sensitive adhesive material layer, respectively. The resulting mixture was coated on a releasing liner made of a polyester in such an amount that the drug content was 400 $\mu g/cm^2$, and then dried to prepare a pressure-sensitive adhesive material layer.

This pressure-sensitive adhesive material layer was transferred to an ethylene-vinyl acetate copolymer film (vinyl acetate content: 28 wt%) having a thickness of 30 $\mu m$ to produce an anti-inflammatory analgesic adhesive preparation of the present invention.

EXAMPLE 4

The anti-inflammatory analgesic adhesive preparation was prepared in the same manner as in Example 3 except that sodium meclofenamate and citric acid were added to the copolymer solution in such amounts that the contents of sodium meclofenamate and citric acid after drying were 20 wt% and 6 wt%, respectively and the resulting mixture was coated on a releasing liner made of a polyester in such an amount that the dry content was 800 $\mu g/cm^2$ and dried to prepare a pressure-sensitive adhesive material layer.

EXAMPLE 5

A mixture of 80 parts of 2-ethylhexyl acrylate and 20 parts of vinyl acetate was copolymerized in the same manner as in Example 1.

To the copolymer solution thus obtained were added fenoprofen calcium and tartaric acid in such amounts that the contents of fenoprofen calcium and tartaric acid after drying were 30 wt% and 9 wt%, respectively. The resulting mixture was coated on a releasing liner made of a polyester in such an amount that the drug content was 600 $\mu g/cm^2$, and then dried to prepare a pressure-sensitive adhesive material layer.

This pressure-sensitive adhesive material layer was transferred to a polyethylene film having a thickness of 30 $\mu m$ to produce an anti-inflammatory analgesic adhesive preparation of the present invention.

EXAMPLE 6

20 Parts of polyisobutyrene rubber (viscosity-average molecular weight: 1,200,000), 30 parts of polyisobutylene rubber (viscosity-average molecular weight: 35,000), 20 parts of polybutene and 30 parts of wood resin were dissolved in a toluene/ethyl acetate (volume ratio: 2/1) mixed solvent and mixed. To the 20% adhesive solution thus obtained were added zomepirac sodium and citric acid in such amounts that the contents of zomepirac sodium and citric acid after drying were 10 wt% and 2 wt%, respectively. The resulting mixture was coated on a releasing liner made of a polyester in such an amount that the drug content was 400 $\mu g/cm^2$, and then dried to prepare a pressure-sensitive adhesive material layer.

This pressure-sensitive adhesive material layer was transferred to a polyethylene film having a thickness of 30 μm to produce an anti-inflammatory analgesic adhesive preparation of the present invention.

EXAMPLE 7

100 Parts of isoprene rubber (molecular weight: 840,000), 30 parts of polybutene (molecular weight: 1,260) and 80 parts of an alicyclic saturated hydrocarbon resin (molecular weight: about 700; melting point: 100° C.) were dissolved in toluene and mixed.

To the 20 wt% adhesive solution thus obtained were added aluminum flufenamate and salicylic acid in such amounts that the contents of aluminum flufenamate and salicylic acid after drying were 20 wt% and 10 wt% based on the pressure-sensitive adhesive material layer, respectively, and the resulting mixture was coated on an ethylene-vinyl acetate copolymer film (vinyl acetate content: 19 wt%) having a thickness of 30 μm in such an amount that the drug content was 800 μg/cm² to form a pressure-sensitive adhesive material layer, thereby preparing an anti-inflammatory analgesic adhesive preparation of the present invention.

COMPARATIVE EXAMPLES 1 TO 5

The anti-inflammatory analgesic adhesive preparation was prepared in the same method as in Examples 1, 3, 5, 6 and 7 (which correspond Comparative Examples 1 to 5, respectively) except that citric acid, succinic acid, tartaric acid or salicylic acid as the organic acid was not used.

TEST EXAMPLE 1

Using the anti-inflammatory analgesic adhesive preparations obtained in each of Examples and Comparative Examples, the inhibition effect of carrageenin foot edema was measured.

The results obtained are shown in Table 1 below.

TABLE 1

|  | Volume of Foot Edema ± S.D. | Inhibition Ratio of Edema (%) |
|---|---|---|
| No Treatment (Control) | 1.25 ± 0.13 | — |
| Example 1 | 0.45 ± 0.09 | 64.0 |
| Example 2 | 0.46 ± 0.15 | 63.2 |
| Example 3 | 0.51 ± 0.11 | 59.2 |
| Example 4 | 0.39 ± 0.10 | 68.8 |
| Example 5 | 0.56 ± 0.13 | 55.2 |
| Example 6 | 0.58 ± 0.18 | 53.6 |
| Example 7 | 0.49 ± 0.08 | 60.8 |
| Comparative Example 1 | 0.80 ± 0.16 | 36.0 |
| Comparative Example 2 | 0.89 ± 0.19 | 28.8 |
| Comparative Example 3 | 0.83 ± 0.13 | 33.6 |
| Comparative Example 4 | 0.94 ± 0.20 | 24.8 |
| Comparative Example 5 | 0.86 ± 0.13 | 31.2 |

Test Method

WS rats (weight: about 180 g) were used. The number of animals was that each group consisted of 10 rats.

The volume of the right hind foot of each rat was measured, and a sample patch (1×2 cm) was applied onto the right hind footpad. After 2 hours, the sample was removed, and 0.05 ml of a 0.5% solution of carrageenin in physiological saline was subcutaneously injected in the same right hind footpad. Three hours after the injection, the volume of the right hind foot was measured. The difference in the volume of the right hind foot between before and after applying of the sample patch was defined as a volume of foot edema.

The inhibition ratio of carrageenin foot edema was calculated by the following equation.

$$\text{Inhibition Ratio of Foot Edema} = \frac{V_c - V_t}{V_c} \times 100$$

wherein $V_c$ represents the average volume of foot edema in a control group, and $V_t$ represents the average volume of foot edema in the group in which the test sample patch was applied.

TEST EXAMPLE 2

The transfer percentage and the transfer amount of the anti-inflammatory analgesic agent when the same adhesive preparations as used in Test Example 1 each was applied to the skin of a human body were measured.

The results obtained are shown in Table 2 below.

Test Method

A test sample (3×4.5 cm) was applied to the back of a human body for 24 hours and then peeled off. The residual anti-inflammatory analgesic agent was extracted with methanol, the transfer percentage and the transfer amount of the agent to the skin surface were calculated from the initial content. Each value in Table 2 is an average value of five subjects.

TABLE 2

|  | Transfer Percentage (%) | Transfer Amount (μg/cm²) |
|---|---|---|
| Example 1 | 15.9 | 66.8 |
| Example 2 | 15.2 | 62.3 |
| Example 3 | 9.5 | 40.5 |
| Example 4 | 9.9 | 78.2 |
| Example 5 | 11.6 | 69.2 |
| Example 6 | 8.3 | 35.0 |
| Example 7 | 11.4 | 90.1 |
| Comparative Example 1 | 3.2 | 13.4 |
| Comparative Example 2 | 2.6 | 11.1 |
| Comparative Example 3 | 3.1 | 18.6 |
| Comparative Example 4 | 1.4 | 5.9 |
| Comparative Example 5 | 2.9 | 22.9 |

It can be seen from the results shown in Tables 1 and 2 that the adhesive preparation of the present invention can provide higher anti-inflammatory effect and greater drug transfer amount of the human skin as compared to the Comparative Examples. Therefore, the adhesive preparation of the present invention is effective in the treatment of diseases.

While the invention has been described in detail and with reference to specific embodiments thereof, it will be apparent to one skilled in the art that various changes and modifications can be made therein without departing from the spirit and scope thereof.

What is claimed is:

1. An anti-inflammatory analgesic adhesive preparation comprising a flexible support having laminated thereon a pressure-sensitive adhesive material layer which contains a non-steroidal anti-inflammatory analgesic agent having a salt form and a pharmaceutically acceptable organic carboxylic acid.

2. The preparation as in claim 1, wherein the non-steroidal anti-inflammatory analgesic agent having a salt form is at least one member selected from the group consisting of tolmetin sodium fenoprofen calcium, sodium meclofenamate, amfenac sodium, zomepirac sodium, loxoprofen sodium, and aluminum flufenamate.

3. The preparation as in claim 1, wherein the carboxylic acid is selected from the group consisting of citric acid, succinic acid, tartaric acid, maleic acid, fumaric acid, salicylic acid and acetic acid.

4. The preparation as in claim 1, wherein the amount of the organic acid is 5 to 100 parts by weight per 100 parts by weight of the non-steroidal anti-inflammatory analgesic agent having a salt form.

5. The preparation as in claim 4, wherein the amount of the organic acid is 10 to 50 parts by weight per 100 parts by weight of the non-steroidal anti-inflammatory analgesic agent having a salt form.

6. The preparation as in claim 1, wherein the amount of the non-steroidal anti-inflammatory analgesic agent having a salt form is 1 to 40% by weight based on the weight of the pressure-sensitive adhesive material.

7. The preparation as in claim 6, wherein the amount of the non-steroidal anti-inflammatory analgesic agent having a salt form is 5 to 30% by weight based on the weight of the pressure-sensitive adhesive material.

8. The preparation as in claim 1, wherein the amount of the non-steroidal anti-inflammatory analgesic agent having a salt form is 20 to 1,600 $\mu g/cm^2$.

9. The preparation as in claim 8, wherein the amount of the non-steroidal anti-inflammatory analgesic agent having a salt form is 100 to 1,200 $\mu g/cm^2$.

10. The preparation as in claim 1, wherein the pressure-sensitive adhesive material is an acrylic pressure-sensitive adhesive material.

11. The preparation as in claim 10, wherein the acrylic pressure-sensitive adhesive material is a copolymer of an alkyl ester of (meth)acrylic acid, an alkyl ester of (meth)acrylic acid containing an ether bond in the molecule, and other copolymerizable monomer.

12. The preparation as in claim 11, wherein the proportion of the alkyl ester of (meth)acrylic acid/the alkyl ester of (meth)acrylic acid containing an ether bond in the molecular/the other copolymerizable monomer is 40 to 80/59 to 10/1 to 40.

* * * * *